United States Patent
Iyengar et al.

(10) Patent No.: US 9,282,891 B2
(45) Date of Patent: Mar. 15, 2016

(54) MONITORING INTRA OCULAR PRESSURE USING PATTERN AND COLOR CHANGES

(76) Inventors: Sundaraja Sitaram Iyengar, Miami, FL (US); Ashwin Kumar Krishna Prasad, Bangalore (IN); Veneeth Iyengar, Miami, FL (US); Krishna Prasad Panduranga Revankar, Bangalore (IN)

(*) Notice: Subject to any disclaimer, the term of this patent is extended or adjusted under 35 U.S.C. 154(b) by 369 days.

(21) Appl. No.: 13/138,316
(22) PCT Filed: Feb. 1, 2010
(86) PCT No.: PCT/IN2010/000054
§ 371 (c)(1),
(2), (4) Date: Aug. 1, 2011
(87) PCT Pub. No.: WO2010/100654
PCT Pub. Date: Sep. 10, 2010

(65) Prior Publication Data
US 2011/0288396 A1    Nov. 24, 2011

(30) Foreign Application Priority Data
Jan. 30, 2009   (IN) .............................. 221/CHE/2009

(51) Int. Cl.
*A61B 3/16*       (2006.01)
*A61B 5/00*       (2006.01)
(Continued)

(52) U.S. Cl.
CPC ... *A61B 3/16* (2013.01); *A61F 2/14* (2013.01); *A61F 2/16* (2013.01); *A61F 9/0017* (2013.01); *A61F 9/00781* (2013.01); *A61K 9/0051* (2013.01)

(58) Field of Classification Search
CPC .... A61B 2562/0247; A61B 3/16; A61B 5/03; A61B 5/036; A61B 5/00; G01L 7/026; G01L 1/24; G01L 1/241; G01L 1/246; G01L 7/086; G01L 7/045; G01L 7/065; G01L 7/106; G01L 7/187

USPC ......... 600/398, 561; 73/729.2, 386, 730, 731; 116/270
See application file for complete search history.

(56) References Cited

U.S. PATENT DOCUMENTS 3,675,722 A * 7/1972 Balmes, Sr. ..................... 169/30
6,597,461 B1 * 7/2003 Verma et al. .................. 356/519
(Continued)

FOREIGN PATENT DOCUMENTS

| WO | 03073959   | 9/2003 |
| WO | 2004062480 | 7/2004 |
| WO | 2007060648 | 5/2007 |

OTHER PUBLICATIONS

Fontecchio, et al. "Proof-of-Concept for Optical Pressure Sensor to Detect Glaucoma." Available online Jul. 3, 2009. Nanophotonics.ece.drexel.edu. 1 page.*
(Continued)

*Primary Examiner* — Rene Towa
*Assistant Examiner* — May Abouelela
(74) *Attorney, Agent, or Firm* — Fleit Gibbons Gutman Bongini & Bianco PL; Gary S. Winer; Paul D. Bianco

(57) ABSTRACT

A Device which enables a person to see for himself changes in Intra Ocular Pressure when he looks at his eye in the Mirror, in the routine course of everyday, as every one likes to see his Own face and eyes in the Mirror everyday. The device being Tiny and inserted surgically with minimum incision between Iris and Cornea, enables early indication of IOP in people with high risk of Glaucoma due to high blood pressure and genetic reasons and old age, the early indication enabling timely treatment before retinal damage. The device works on pattern changes due to pressure change which is compared with fixed background pattern and changes in spacing between lines of Diffraction grating and Hologram leading to color changes due to interference effect of light. Mirror with an area of concave surface and Magnifying device along with comparison Chart enables proper monitoring of drug efficacy.

16 Claims, 2 Drawing Sheets

(51) Int. Cl.
*A61F 9/00* (2006.01)
*A61F 2/14* (2006.01)
*A61F 2/16* (2006.01)
*A61F 9/007* (2006.01)
*A61K 9/00* (2006.01)

(56) References Cited

U.S. PATENT DOCUMENTS

| | | | |
|---|---|---|---|
| 6,778,236 B1* | 8/2004 | Crawford et al. | 349/86 |
| 6,817,311 B1* | 11/2004 | Treen et al. | 116/270 |
| 7,654,957 B2* | 2/2010 | Abreu | 600/399 |
| 8,298,156 B2* | 10/2012 | Manstrom et al. | 600/561 |
| 2004/0254438 A1* | 12/2004 | Chuck et al. | 600/398 |
| 2005/0113913 A1 | 5/2005 | Duvert | |
| 2005/0232532 A1* | 10/2005 | Wang et al. | 385/13 |
| 2005/0256570 A1* | 11/2005 | Azar | 623/5.14 |
| 2005/0268722 A1* | 12/2005 | Tai et al. | 73/715 |
| 2006/0247664 A1 | 11/2006 | Meng et al. | |
| 2007/0019156 A1* | 1/2007 | Fink | 351/200 |
| 2007/0142718 A1* | 6/2007 | Abreu | 600/323 |
| 2009/0004245 A1* | 1/2009 | Orilla et al. | 424/429 |
| 2009/0266145 A1 | 10/2009 | Naydenova | |
| 2011/0160561 A1* | 6/2011 | Hastings et al. | 600/398 |

OTHER PUBLICATIONS

International Search REeport for PCT/IN2010/000054 dated Sep. 9, 2010.
International Preliminary Report on Patentability for PCT/IN2010/000054 dated Aug. 2, 2011.
Written Opinion for PCT/IN2010/000054 dated Aug. 30, 2010.
Interferometry, Wikipedia, Mar. 19, 2014.
Holographically Formed Polymer Dispersed Liquid Crystals, Mar. 19, 2014, Drexel Nanophotonics+ Lab.
Proof-of-Concept for Optical Intraocular Pressure Sensor to Detect Glaucoma, Nov. 19, 2013, Drexel.
Proof-of-Concept for Optical Intraocular Pressure Sensor to Detect Glaucoma, Mar. 17, 2014, Drexel.
Moire pattern, term Wikipedia, pp. 7, retrieved Dec. 22, 2014.

\* cited by examiner

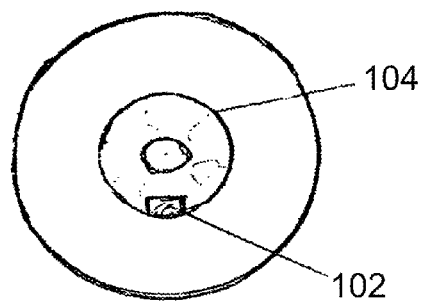
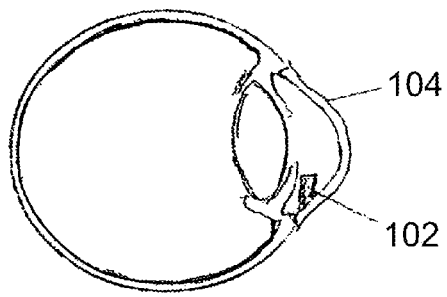
FIG. 1   FIG. 2
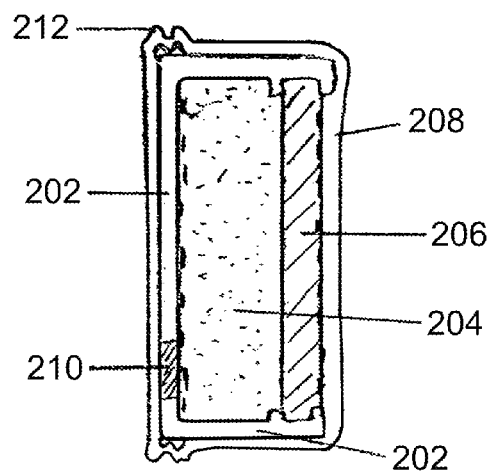
FIG. 3
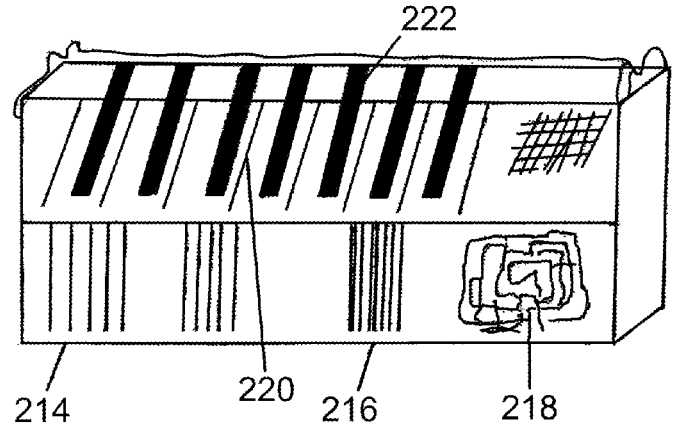
FIG. 4

MONITORING INTRA OCULAR PRESSURE USING PATTERN AND COLOR CHANGES

CLAIMS OF PRIORITY

This patent application claims priority from the Provisional Patent Application No221/CHE/2009 titled . . . Device to indicate pressure in eye due to glaucoma by means of Optical changes filed on 30th Jan. 2009.

FIELD OF TECHNOLOGY

This disclosure relates generally to technical field of Ophthalmology in the early detection and monitoring of Intra Ocular Pressure, which could lead to Glaucoma in people who have a high risk of getting Glaucoma such as diabetics, people above 50 years with high blood pressure. The monitoring enables timely treatment by Ophthalmologists there by reducing retinal damage.

SUMMARY

Background of Invention

Glaucoma is a silent enemy to mankind, which stealthily damages the retina with out giving indications to the person. So the purpose of this invention is to see that the silent damage is detected as far as possible well ahead of the damage, specially in people who are at high risk getting their retina damaged by increased Intra Ocular Pressure like people with high blood pressure and genetic history of Glaucoma. The presently available methods for measuring Intra Ocular Pressure such as Tonometry based on applanation both contact and non contact types, requires the person to go to a Ophthalmologist for check up which the person will usually do after a good portion of retina is already irreversible damaged. Devices with implantable pressure sensors based on electrical resistance measurement have cumbersome interface and display.

The present device allows a person in the high risk group to monitor Intra Ocular Pressure by himself or herself, since everybody will invariably look at his or her own face and eyes every day in the Mirror and can notice changes in pattern and colour of the implanted devise which is a tiny strip and seek timely expert help from Ophthalmologists. The device further helps in monitoring the efficacy of the drugs used in treatment to lower Intra ocular pressure and allows necessary changes in drugs and its dosage so that Intra Ocular Pressure is brought to acceptable level.

The device makes use of the property of elastomers to change in shape due to pressure change leading to change in patterns present on their surface. This change in pressure can be observed by the person himself or herself as change in colour and change in pattern indicating the increase in pressure thereby prompting timely action by contacting the expert ophthalmologists to help in reducing the pressure, thereby preventing damage of retina due to increased Intra Ocular Pressure in a large percentage of people who's retina get damaged mainly due to increase in Intra Ocular Pressure.

SCOPE OF INVENTION

The device will have served its purpose by preventing a large portion of people who have the risk of getting Glaucoma due to increased Intra Ocular Pressure, getting timely treatment and better monitoring and avoid loss of vision. A vision saved is worth the effort especially when regular monitoring is not undertaken. The loss of vision to the person who has lost vision is so very bad that science and Technology should try to save as many as possible.

The device, systems, and methods disclosed herein may be implemented in any means for achieving various aspects. Other features will be apparent from the accompanying drawings and from the detailed description that follows.

BRIEF DESCRIPTION OF THE DRAWINGS

Example embodiments are illustrated by way of example and not limitation in the figures of the accompanying drawings, in which like references indicate similar elements and in which:

FIG. 1 is Position of the devise in the eye as seen from Front in one embodiment.

FIG. 2 is Position of the device in the Eye shown between the his and Cornea in one embodiment.

FIG. 3 is magnified cross section view of the device according to one embodiment.

FIG. 4 is Magnified front view of the device shows regions of different patterns according to one embodiment.

Figure 5:
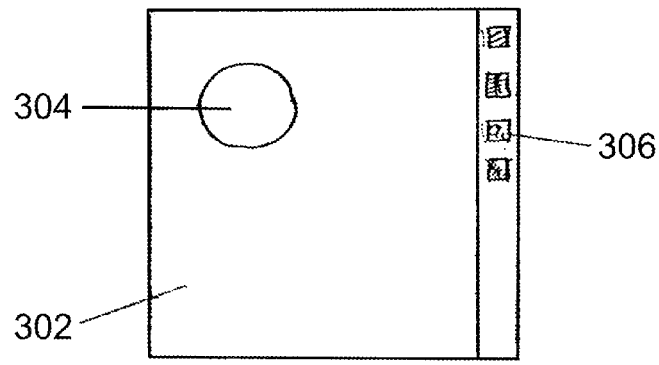
FIG. 5 is Front view of the Mirror with a region of concave surface and comparison chart of Patterns according to one embodiment.

Other features of the present embodiments will be apparent from the accompanying drawings and from the detailed description that follows.

DETAILED DESCRIPTION

A device, system and method to monitor Intra Ocular Pressure by the person himself or herself everyday by looking at the device in a mirror and through magnifier. Although the present embodiments have been described with reference to specific example embodiments, it will be evident that various modifications and changes may be made to these embodiments without departing from the broader spirit and scope of the various embodiments.

FIG. 1 indicates the position of the device in the Eye as seen from front. The device 102 is placed behind the Cornea and in front of the Iris, according to one embodiment.

FIG. 2 indicates the position of the device inside the eye. The device 102 is between the Iris and the Cornea, according to one embodiment.

FIG. 3 is the Magnified cross section view of the device. In the example embodiment the Rigid Base 202 is made of plastic material. The background fixed pattern is present on the rigid base 202. A magnetic strip 210 is embedded in the Rigid base 202. To the rigid base 202 is attached Elastomer layer 206 which stretches due to pressure changes. The Elastomer layer 206 has the patterns which change. Between Rigid base 202 and Elastomer layer 206 is a Gel layer 204 which is used to enhance sensitivity of the device to pressure. The entire device is surrounded by a transparent bio compatible polymer layer 208 which has folds at the back shown as 212 to give flexibility so that the elastomer layer 206 can stretch in response to pressure changes. The elastomer layer 206 is positioned initially taking base line pressure agreed upon by expert Ophthalmologists, according to one embodiment FIG. 4 is a Magnified Front view of the device in the example embodiment. The pattern 214 on the Elastomer layer 206 is a diffraction grating with lines of suitable spacing, the Pattern 216 on the Elastomer layer 206 is a diffraction grating with a different spacing which changes colour for a higher pressure level than the pattern 214. The pattern 218 on the Elastomer 206 is a Hologram that changes colour depending on amount of stretching of elastomer layer 206. The Pattern 220 is the variable pattern on the Elastomer 206 while Pattern 222 is the fixed pattern on Rigid base 202 which serves as a reference to compare changes in Pattern 220 due to pressure changes. The colour of the iris of the person is taken into account for selecting the appropriate patterns.

The above pattern is one of that printed by micro lithography, by one of etching with laser and photo etching, and by one of embossing to give the hologram pattern and diffraction grating and background pattern with its counter pattern.

FIG. 5 is the front view of the Mirror 302 which has a region with Concave surface 304. A comparison Chart 306 is provided to read of the level of intra Ocular Pressure according to one embodiment.

Figure 6:
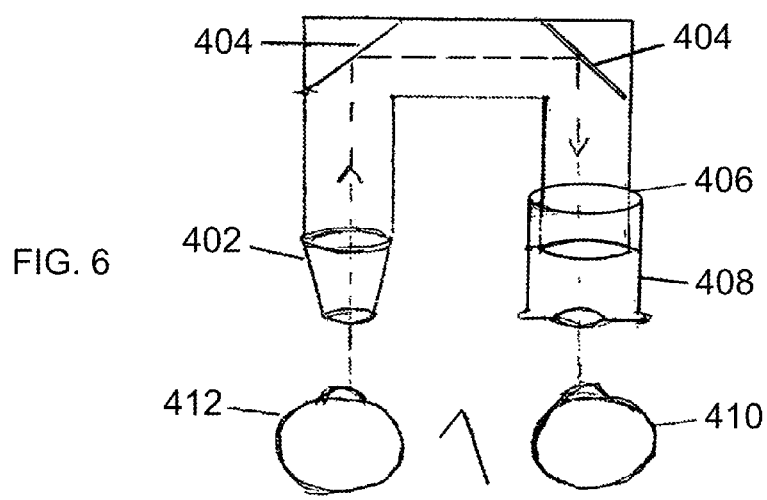
FIG. 6 is schematic of Magnifier arrangement showing Objective lens, mirrors and eyepiece, according to one embodiment.

FIG. 6 is a schematic of the Magnifier arrangement which comprises of an Objective Lens 402, a pair a mirrors 404 positioned a right angles, a screw type groove 406 to move the eyepiece 408 for focusing purpose. The IOP monitoring device in the eye 412 is observed by eye 410. The magnifier is reversed to observe the IOP monitoring devise in eye 410 by eye 412, according to one embodiment. Enhancement to this magnifier can be made to monitor other conditions of the eye if necessary.

Figure 7:
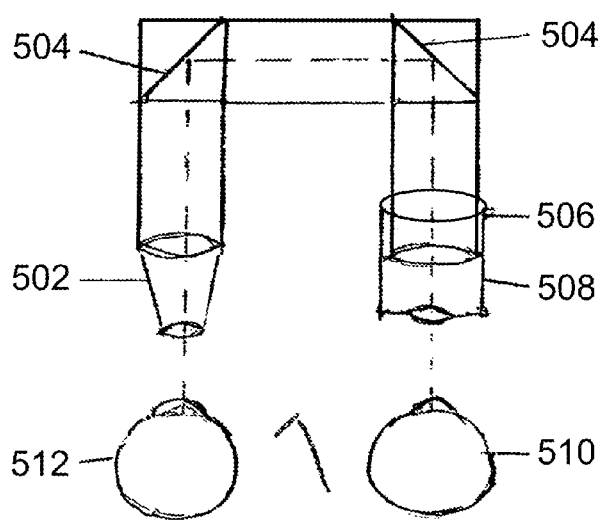
FIG. 7 is schematic of Magnifier arrangement showing objective lens, right angled prisms and Eyepiece, according to one embodiment.

FIG. 7 is a schematic of the Magnifier arrangement which comprises of an Objective Lens 502, a pair a right angled prisms 504, a screw type groove 506 to move the eye piece 508 for focusing purpose. The IOP monitoring device in the eye 512 is observed by eye 510. The magnifier is reversed to observe the IOP monitoring devise in eye 510 by eye 512, according to one embodiment. Enhancement to this magnifier can be made to monitor other conditions of the eye if necessary.

In addition, it will be appreciated that the various operations, processes, and methods disclosed herein may be performed in any order (e.g., including using means for achieving the various operations). Accordingly, the specification and drawings are to be regarded in an illustrative rather than a restrictive sense.

We claim:

1. A device to self monitor intra ocular pressure by a patient, comprising: an ocular implant sized and dimensioned to be placed behind a cornea in the interior of an eye, and including an elastomeric layer; and a pattern of spaced lines on the elastomeric layer forming a visible diffraction grating which changes color as the elastomeric layer together with the spaced lines are stretched due to increased intra ocular pressure, when the implant is located behind the cornea, to indicate a change in intra ocular pressure; further including a device configured to display the eye containing the ocular implant to another eye of the patient, the device uses a mirror to reflect an image of the eye containing the ocular implant towards the other eye.

2. The device of claim 1, further including a second pattern of spaced lines on the elastomeric layer forming a diffraction grating which changes color as the elastomeric layer stretches, the second pattern changing color at a higher intra ocular pressure than the pattern of spaced lines of claim 1.

3. The device of claim 1, wherein the diffraction grating is visible using at least one of the unaided eye and a magnifying lens.

4. A device to self monitor intra ocular pressure by a patient, comprising: an ocular implant sized and dimensioned to be placed behind a cornea in the interior of an eye, and including a rigid base layer having visible lines forming a fixed pattern; and an elastomeric layer connected to the rigid base layer, the elastomeric layer having visible lines forming a variable pattern, the fixed pattern visible through the elastomeric layer, the lines of the fixed pattern thereby forming a reference pattern optically visible by the patient to compare changes in the variable pattern of the elastomeric layer when the elastomeric layer together with the lines are stretched due to a natural change in intra ocular pressure when the implant is located behind the cornea, the compared changes operative to indicate a change in intra ocular pressure; further including a device configured to display the eye containing the ocular implant to another eye of the patient, the device uses a mirror to reflect an image of the eye containing the ocular implant towards the other eye.

5. The device of claim 4, at least one of the fixed and variable pattern formed by one of etching with laser, vapor deposition, sputtering, photo etching, and embossing.

6. The device of claim 4, further including a gel layer positioned between the rigid base layer and the elastomeric layer.

7. The device of claim 4, further including a mirror useable by the patient external to the eyes of the patient and having a portion with a concave surface configured to magnify an image of the implant when the implant is within an eye.

8. The device of claim 4, further including a magnetic object connected to the implant, the magnetic object moveable by magnetic attraction from outside the eye when the implant is implanted within the eye to thereby move the implant within the eye to thereby enable adjustment of the placement of the implant.

9. The device of claim 4, the implant covered by a biocompatible polymer layer.

10. The device of claim 9, the covering biocompatible polymer layer including folds to enable movement of the elastomeric layer.

11. The device of claim 4, further including:
an implant viewer device having
three channels forming a U shape with two open ends, one of the two ends positionable in front of an eye of the patient which has the implant implanted, the other of the two ends simultaneously positionable in front of the other eye of the patient; and
two reflectors positioned within the U shape, whereby one eye of the patient can observe the other eye of the patient, and can observe the background pattern image and the counter pattern image of the implant.

12. The device of claim 11, further including an adjustable focusing lens positioned within one of the three channels.

13. The device of claim 11, wherein the reflectors are selected from the group consisting of mirror and prism.

14. The device of claim 4, further including a hologram pattern formed upon the elastomeric layer, an appearance of the hologram changing as intra ocular pressure changes, when the implant is implanted within an eye of the patient.

15. The device of claim 4, further including gel layer positioned between the rigid base layer and the elastomeric layer.

16. The device of claim 4, wherein the reference pattern optically visible by the patient is optically visible using at least one of the unaided eye and a magnifying lens.

* * * * *